(12) United States Patent
Silverberg et al.

(10) Patent No.: US 9,615,823 B2
(45) Date of Patent: Apr. 11, 2017

(54) TOOLS AND METHODS FOR REMOVING ANCHORS FROM MEDICAL LEADS

(75) Inventors: Jacob W. Silverberg, Blaine, MN (US); Michael J. Kern, St. Louis Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 453 days.

(21) Appl. No.: 13/356,050

(22) Filed: Jan. 23, 2012

(65) Prior Publication Data

US 2012/0197264 A1 Aug. 2, 2012

Related U.S. Application Data

(60) Provisional application No. 61/436,986, filed on Jan. 27, 2011.

(51) Int. Cl.
*A61B 19/00* (2006.01)
*A61B 17/04* (2006.01)
*A61N 1/05* (2006.01)

(52) U.S. Cl.
CPC .......... *A61B 17/0467* (2013.01); *A61N 1/057* (2013.01); *A61B 2017/0411* (2013.01)

(58) Field of Classification Search
CPC .......... A61M 2025/0675; A61M 25/06; A61M 25/0668; A61B 17/32002; A61B 17/320016; A61B 17/320783; A61B 17/32093; A61B 17/3211; A61B 17/1695; A61B 17/0467; A61F 9/0133
USPC ..... 606/76, 80, 83, 169, 170, 171, 172, 174, 606/177, 184, 185, 205, 206, 207; 30/278, 280; 604/161; D24/146, 147
See application file for complete search history.

(56) References Cited

U.S. PATENT DOCUMENTS

| | | | | |
|---|---|---|---|---|
| 2,127,190 | A | * 8/1938 | Solomon | 606/158 |
| 4,553,961 | A | 11/1985 | Pohndorf et al. | |
| 4,997,424 | A | * 3/1991 | Little | A61M 25/0668 30/90.4 |
| 5,007,171 | A | * 4/1991 | Horning, Jr. | 30/294 |
| 5,115,568 | A | * 5/1992 | Aida | 30/294 |
| 5,188,606 | A | * 2/1993 | Maloney | A61M 25/0668 604/161 |
| 5,632,088 | A | 5/1997 | Naso et al. | |
| 5,745,996 | A | 5/1998 | Kenny et al. | |
| 5,843,146 | A | 12/1998 | Cross, Jr. | |
| D467,658 | S | * 12/2002 | Goodwin | D24/133 |
| 6,497,681 | B1 | * 12/2002 | Brenner | A61M 25/0668 604/160 |
| 7,591,970 | B2 | 9/2009 | Olson | |

(Continued)

*Primary Examiner* — Tuan V Nguyen
(74) *Attorney, Agent, or Firm* — Withers & Keys, LLC

(57) ABSTRACT

Tools and methods for removing anchors from medical leads involve a guide portion and a blade. The lead is inserted within a lead passageway of the guide portion of the tool and the tool is moved along so that the blade contacts the anchor and cuts a slit in the anchor as the tool. Once the blade has cut the slit through the entire anchor, the anchor comes free of the lead and the tool can be removed. The tool may include a manner of opening and closing the guide portion so as to provide access to the lead when open and to contain the lead when closed. Opening the guide portion allows the lead to be inserted or removed by laterally moving the lead into or out of the lead passageway such that the tool may be installed or removed at any available point along the lead.

13 Claims, 14 Drawing Sheets

(56) References Cited

U.S. PATENT DOCUMENTS

| | | | |
|---|---|---|---|
| 7,963,040 B2* | 6/2011 | Shan | A61M 25/06 30/90.1 |
| 2003/0229386 A1* | 12/2003 | Rosenman | A61N 1/056 607/116 |
| 2009/0248054 A1 | 10/2009 | Sage et al. | |
| 2011/0138633 A1* | 6/2011 | Mellas et al. | 30/169 |

* cited by examiner

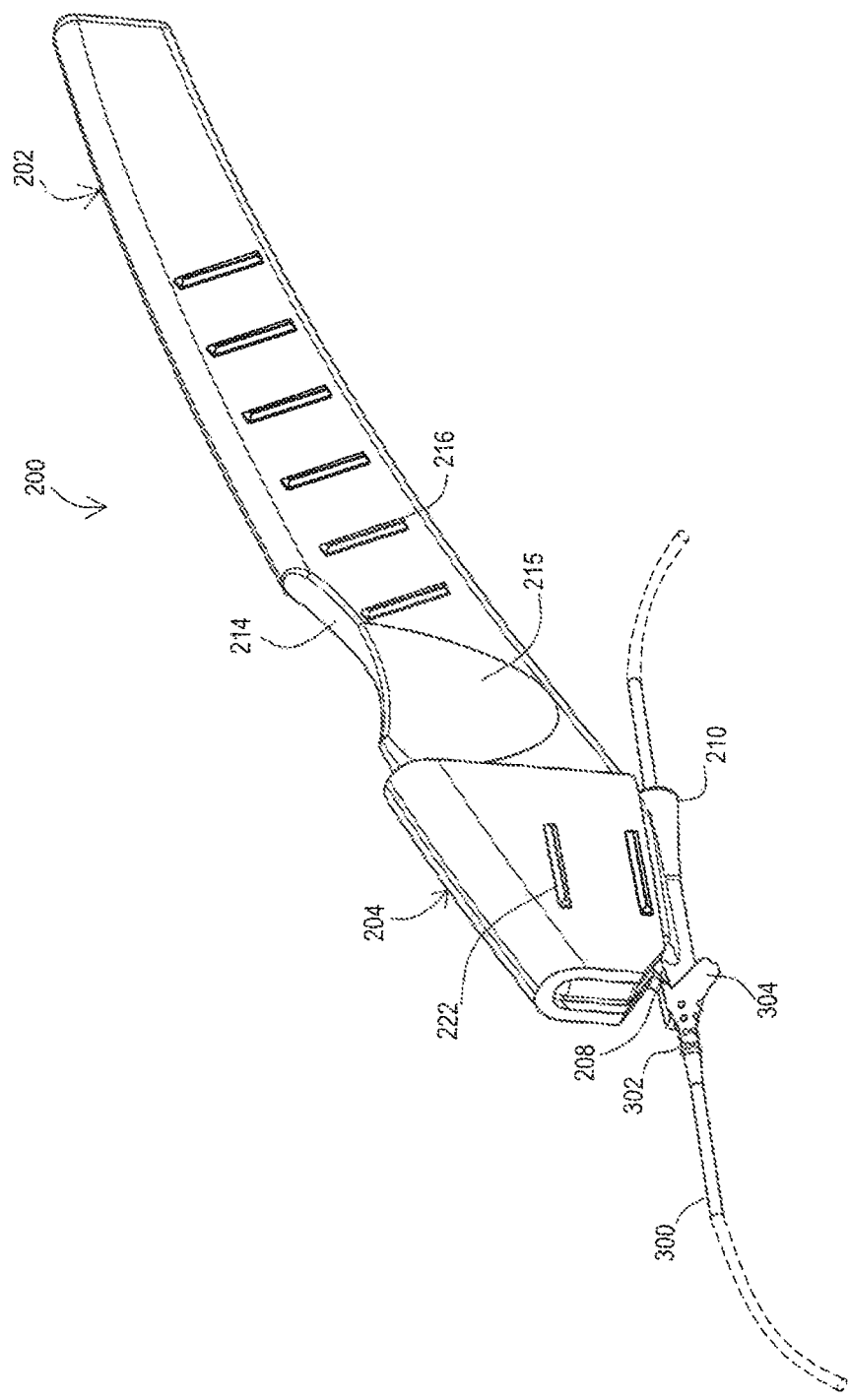

US 9,615,823 B2

TOOLS AND METHODS FOR REMOVING ANCHORS FROM MEDICAL LEADS

RELATED APPLICATION

This application claims priority to U.S. Provisional Patent Application Ser. No. 61/436,986, filed Jan. 27, 2011, which application is incorporated herein in its entirety.

TECHNICAL FIELD

Embodiments are related to the removal of anchors from medical leads. More particularly, embodiments are related to tools and methods for removal of the anchors.

BACKGROUND

Implantable medical devices that produce stimulation signals and/or that sense physiological signals utilize implantable medical leads to carry electrical signals. The implantable medical leads include electrodes on a distal end that interface with the bodily tissue. Electrical conductors within the medical lead electrically connect the electrodes on the distal end with electrical contacts on the proximal end that engage electrical connectors of the medical device.

The medical lead is implanted within the body with the distal end being routed to the appropriate site to stimulate and/or sense. The proximal end of the lead remains nearby the incision site where the medical device is also implanted and sutured to tissue. To ensure that the lead is also held in place, an anchor is installed on the lead, and the anchor is then sutured to tissue.

Conventionally, anchors were designed to slide over the lead body and then be held tightly to the lead body by the suture. In such a case, the anchor could be removed by cutting the suture and then sliding the anchor off of a free end of the lead, typically the proximal end of the lead that is disconnected from the medical device. However, there may be other anchor designs that use elasticity to grip onto the lead body and do not freely slide along the lead body. In that case, cutting the sutures that tie the anchor to the tissue does not result in the anchor being able to slide off of a free end of the lead such that the anchor remains affixed to the lead body.

SUMMARY

Embodiments address issues such as these and others by providing anchor removal tools and methods for removing anchors from a lead body. The embodiments provide for attaching a tool to the lead body by placing the lead within a lead passageway within a guide portion of the anchor tool. The embodiments further provide for sliding the tool along the lead body to engage a blade of the tool against the anchor and to cut through the anchor thereby releasing the anchor from the lead body.

Embodiments provide an implantable medical lead anchor removal tool that includes a first body including a guide portion having an inner lead passageway having a longitudinal dimension. A second body is movably coupled to the first body, the inner lead passageway being opened along the longitudinal dimension when the second body is moved relative to the first body. A blade is present within the first body, and the blade has a cutting edge that is at least partially exposed from the first body and that is aligned so that a plane defined by the blade intersects with the guide portion in the first body.

Embodiments provide a method of removing an anchor from an implantable medical lead that involves opening a lead passageway within a guide portion of an anchor removal tool along a longitudinal dimension of the lead passageway. The method may involve introducing the lead into the opening of the lead passageway along the longitudinal dimension. The method may involve closing the lead passageway within the guide portion of the anchor removal tool once the lead has been introduced into the lead passageway. Additionally, the method may involve sliding the anchor removal tool along the lead with the lead passing through the guide portion such that a blade of the anchor removal tool cuts through the anchor.

DESCRIPTION OF THE DRAWINGS

FIG. 14 shows a side view of the second example being used to remove the anchor from the lead.

DETAILED DESCRIPTION

Embodiments provide anchor removal tools and methods of removing anchors from implantable medical leads. The anchor removal tools include a blade that is used to cut through the anchor while also including a lead passageway that the lead passes through as the tool is removing the anchor from the lead. The anchor removal tools may provide structures for opening and closing access to the lead passageway such that the lead can be inserted into the lead passageway when open and may then be captured within the lead passageway when closed where the anchor tool may then move along the lead without the lead coming free from the lead passageway.

Figure 1:
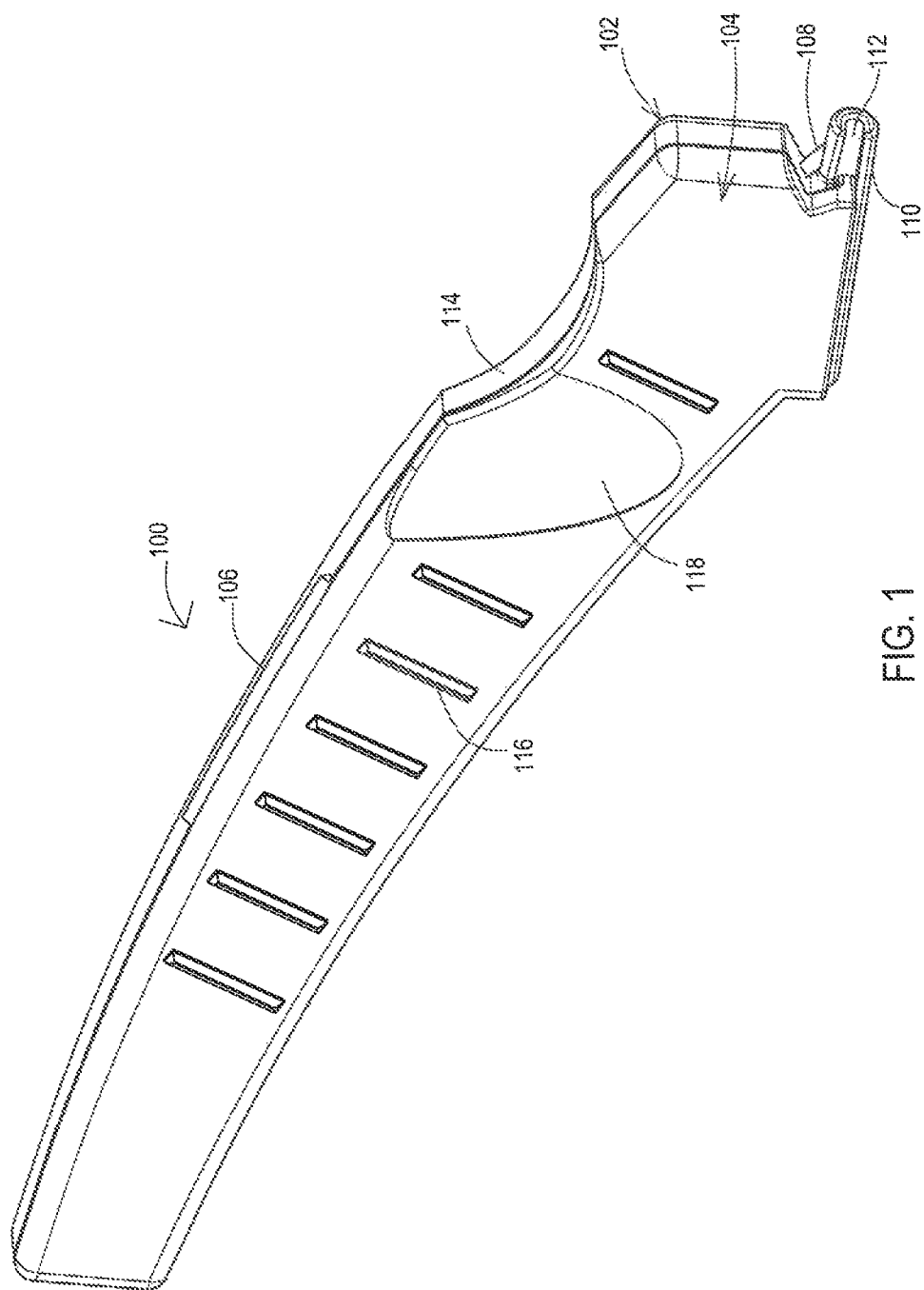
FIG. 1 shows a side view of an example of an anchor removal tool according when in a closed position.

FIG. 1 shows one example of an anchor removal tool 100 in a closed position. The anchor removal tool 100 includes a first body 102 and a second body 104 that are coupled together by a hinged coupling 106. In this particular example, the first body 102, second body 104, and the hinged coupling 106 are integral to one piece of material of the tool 100, but it will be appreciated that one or more of these could be a separate piece that is attached to an adjacent piece. In this example, the one piece of material is formed such that the hinged coupling 106 has a relatively thin construction so as to sharply bend to provide the hinge function. The hinged coupling 106 may have a normal state that the hinged coupling 106 is biased toward, such as the open position so that when released from the closed position by the user the tool 100 begins to open about the hinged coupling 106. The first and second bodies 102, 104 and the hinged coupling 106 may be made of various rigid materials such as various types of a polymer like polypropylene.

The first body 102 houses a blade 108 that is at least partially exposed such that a cutting edge of the blade 108 is also exposed. The cutting edge of the blade 108 ultimately contacts the anchor to slice through the anchor and ultimately release the anchor from the lead body. The blade 108 may be made of a rigid material capable of having a cutting edge suitable for cutting through an anchor material like silicone rubber. For instance, the blade 108 may be various types of metal like stainless steel. The first body 102 may be molded about the blade 108 or the blade 108 may be otherwise installed within a compartment within the first body 102.

The first body 102 of this example also includes a guide portion 110 which serves to guide the tool 100 along the lead body. The guide portion 110 defines the lead passageway 112 where the lead is placed. The lead slides through the lead passageway 112 as the tool 100 moves along the lead to approach and cut through the anchor.

The second body 104 closes the lead passageway 112 so that the lead cannot move laterally out of the lead passageway 112 but can only slide in the longitudinal dimension of the lead passageway 112. Thus, the presence of the second body 104 ensures that the lead remains within the lead passageway 112 as the tool 100 slides along the lead to approach and cut through the anchor.

To assist the user in sliding the tool 100 along the lead and through the anchor, the first and second bodies 102, 104 include protrusions 116 that allow the user to obtain a better grip on the tool 100. The protrusions 116 are oriented at an angle relative to the longitudinal dimension of the lead passageway 112 such that when force is applied by the user in the longitudinal dimension of the guide portion 110 in order to move the tool 100 and cut the anchor, the protrusions 116 provide a surface that opposes slippage of the grip by the user.

Figure 2:
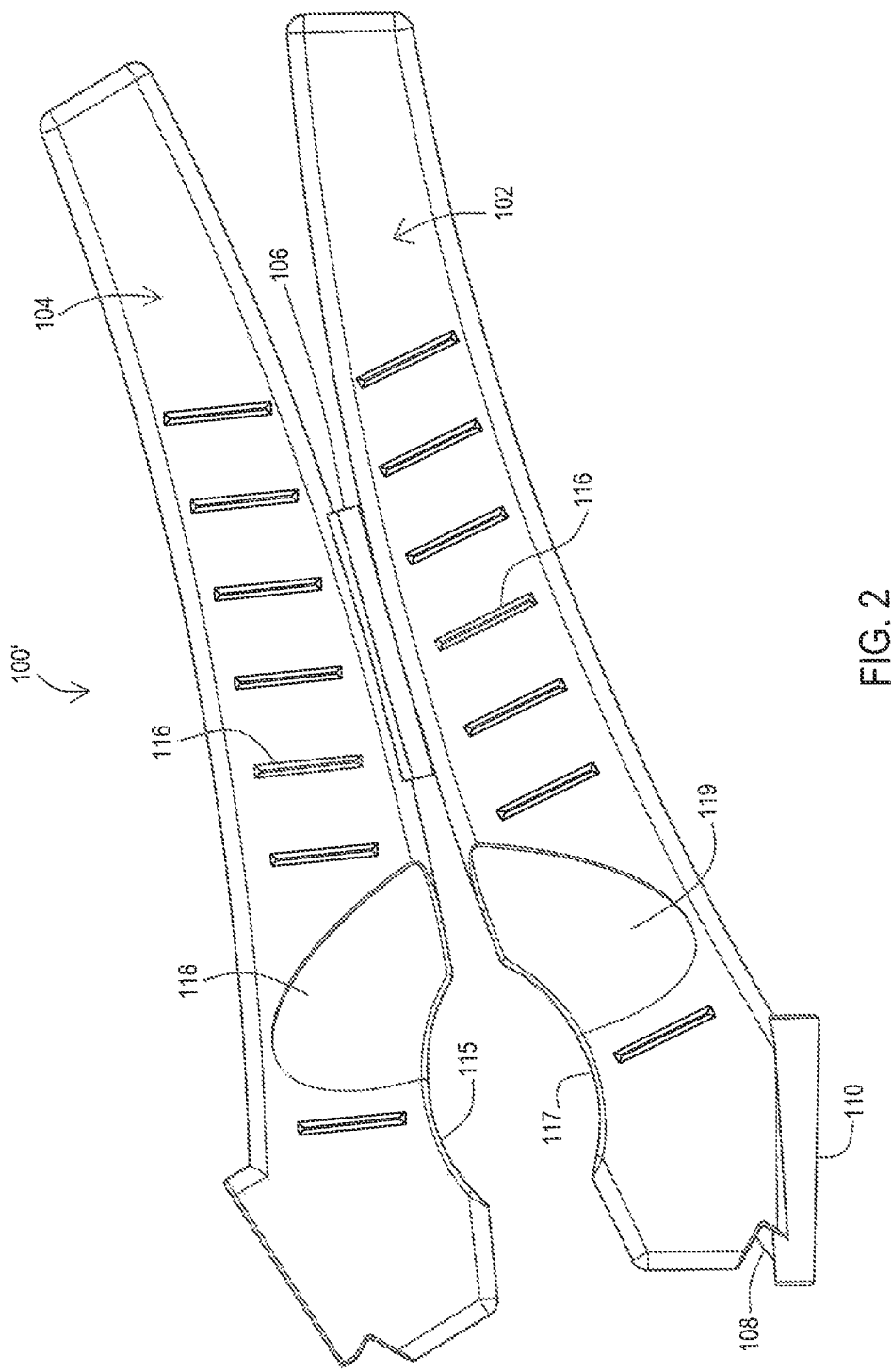
FIG. 2 shows a side view of the example in an open position.
Figure 6:
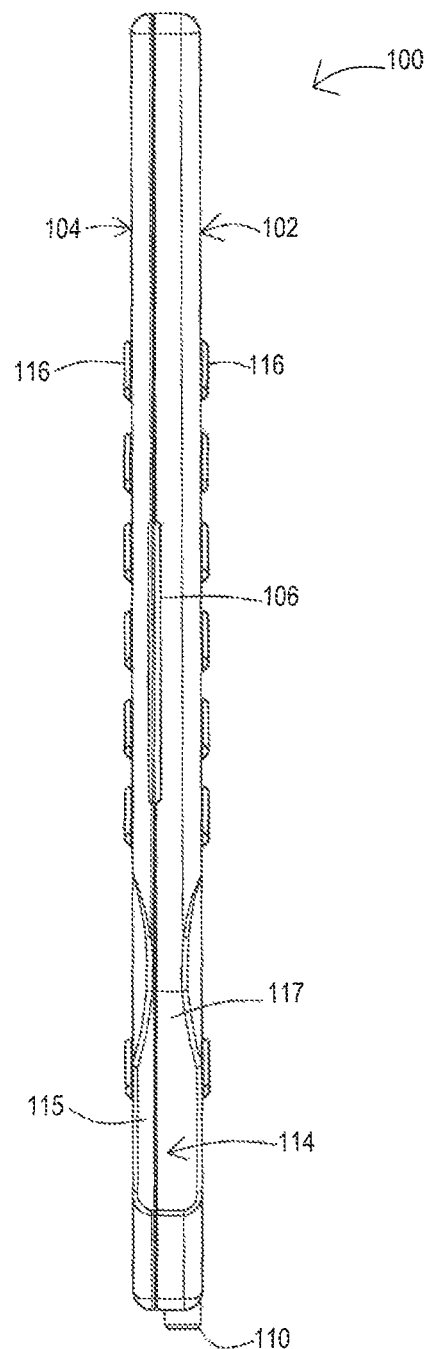
FIG. 6 shows a top view of the example in the closed position.

To further assist the user in sliding the tool 100, the first and second bodies 102, 104 include side indentations 118, 119, as shown in FIG. 2, that are shaped to receive the pinch of a finger and thumb. The first and second bodies 102, 104 may include edge indentations 115, 117 along a top edge which form a common indentation 114 when the second body 104 is closed relative to the first body 102 as in FIG. 1. The alignment of the indentations 115 and 117 to form the common indentation 114 can be seen in the top view of FIG. 6. The edge indentation 114 may also be shaped to receive a finger such as where the user prefers to press on the top edge with a thumb or pointer finger when sliding the tool 100.

Figure 3:
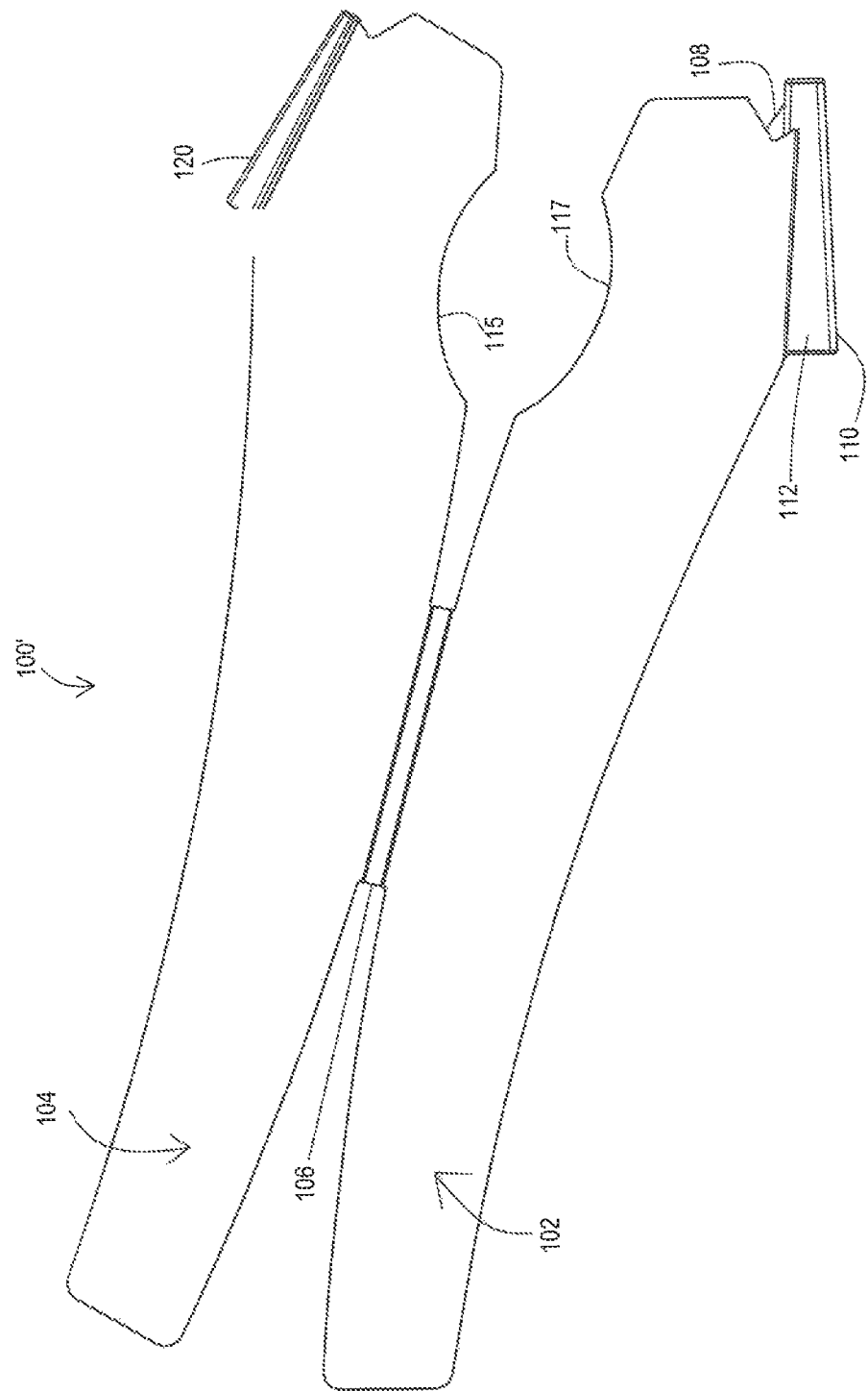
FIG. 3 shows an opposite side view of the example in the open position.

FIG. 2 shows an open tool 100' from one side while FIG. 3 shows the open tool 100' from the opposite side. This example includes arcuate shapes for the first and second bodies 102, 104 which form an arcuate handle in the closed position as shown in FIG. 1. Here the second body 104 has been opened from the first body 102 by rotation of the second body 104 relative to the first body 102 at the hinged coupling 106. The result of opening the second body 104 relative to the first body 102 is that the lead passageway 112 within the guide portion 110 is open along the longitudinal dimension of the lead passageway 112 as seen most clearly in FIG. 3. This opening of the lead passageway 112 allows the lead to be inserted by lateral movement of the lead and thus at any available point along the lead rather than requiring the proximal or distal end of the lead to be inserted axially into the lead passageway 112. In this particular example, the second body 104 includes a guide portion 120 that cooperates with the guide portion 110 to further close the lead passageway 112 when the second body 104 is closed relative to the first body 102.

FIG. 3 also shows that the guide portion 110 and lead passageway 112 of this example have a taper. The small diameter end of the taper is at the front of the tool 100 that approaches the anchor. Thus, the small diameter end of the taper of the guide portion 110 allows the guide portion 110 to begin to slide between the lead body and the anchor as the tool 100 is pressed forward into the anchor. As the anchor slides up the tapered end of the guide portion 110, the anchor encounters the blade 108 which begins to cut through the anchor. As the lead passageway 112 tapers to a larger diameter, there is less drag created due to less impactful contact with the length of the lead body within the lead passageway 112.

Figure 4:
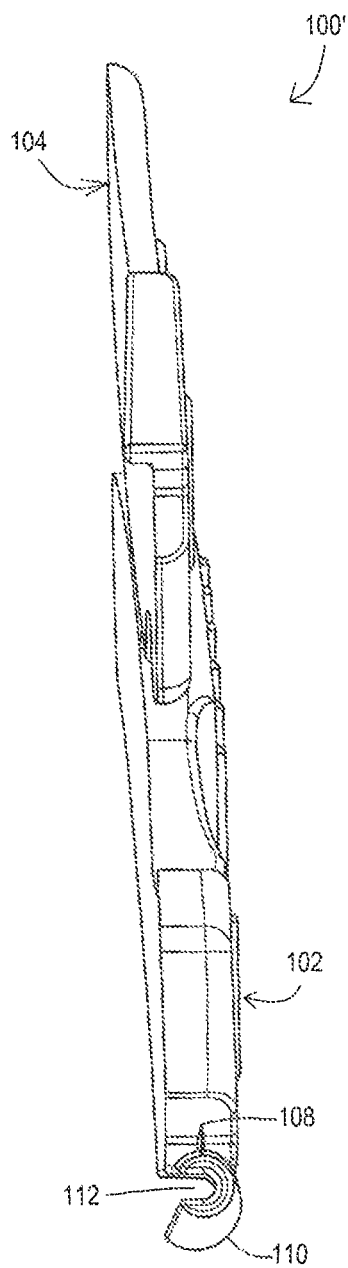
FIG. 4 shows a front view of the example in the open position.

FIG. 4 shows a front view of the opened tool 100' where the relationship of the blade 108 to the guide portion 110 and lead passageway 112 is further depicted. Here it can be seen that a plane created by the blade 108 intersects with the guide portion 110 so as to completely cut through the anchor that is encountering the guide portion 110. In this particular example, the plane of the blade 108 also intersects with the lead passageway 112 to create a more radial cut through the anchor. The open side of the lead passageway 112 which allows the lead to be inserted by moving the lead in a lateral direction, and thus at any available point along the lead, can also be seen in FIG. 4.

Figure 5:
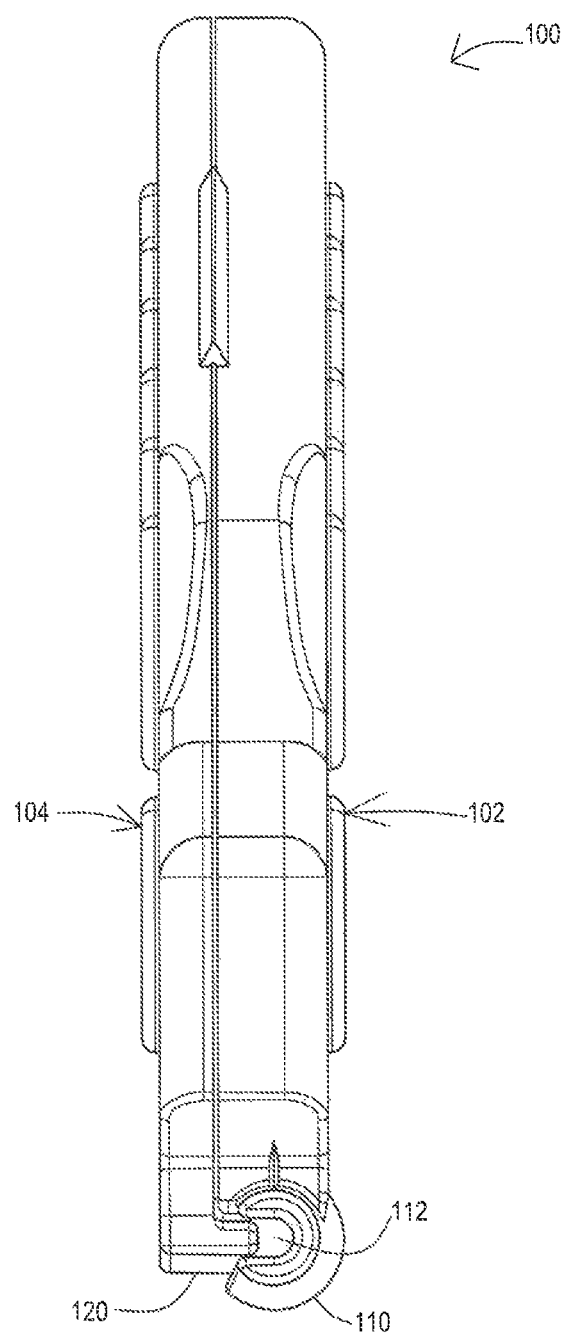
FIG. 5 shows a front view of the example in the closed position.

FIG. 5 shows a front view of the closed tool 100. Here the relationship of the blade 108, the guide portion 110 of the first body 102 and the guide portion 120 of the second body 104 can be seen. The guide portion 120 closes the longitudinal opening to the lead passageway 112 within the guide portion 110 so as to create an enclosed path for the lead which also isolates the lead from the blade 108.

Figure 7:
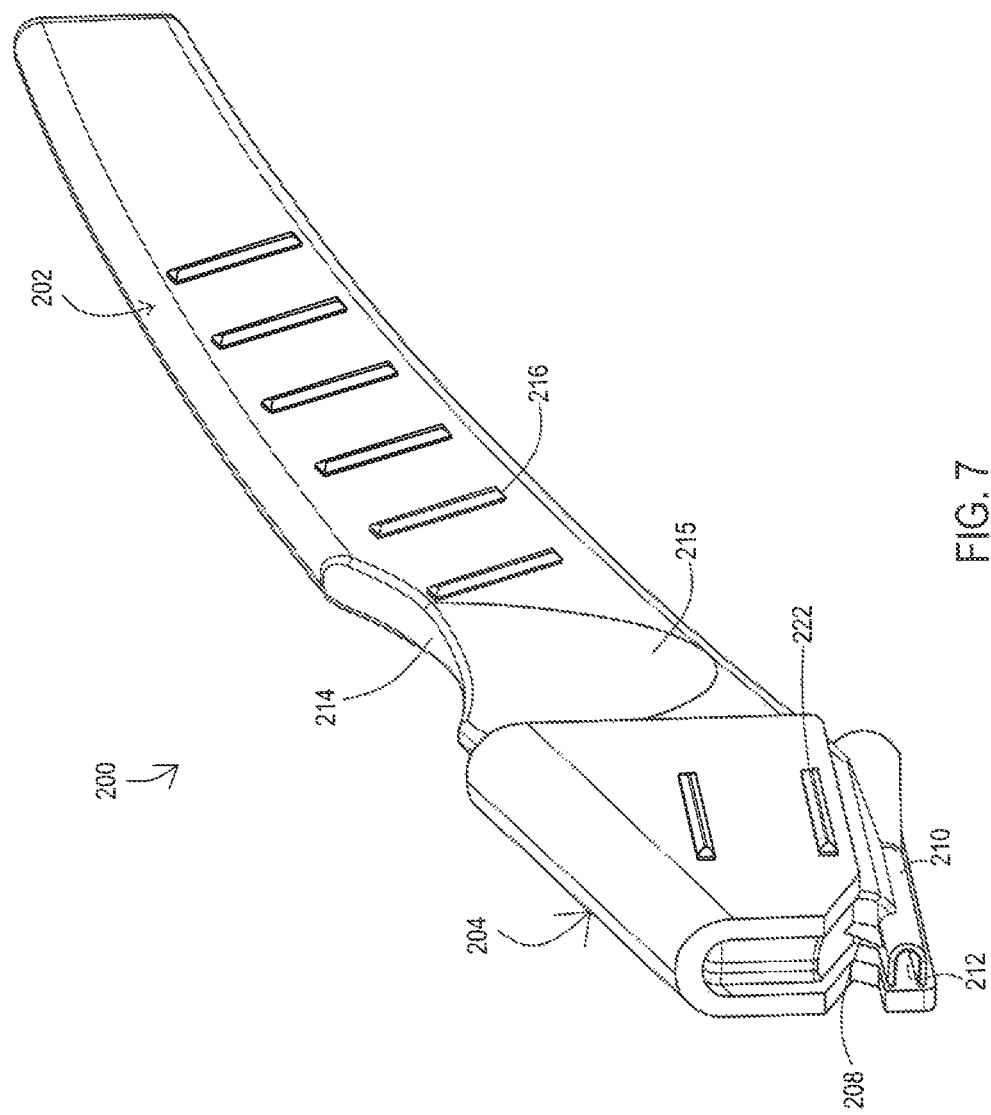
FIG. 7 shows a side view of a second example with a clip in a closed position.
Figure 10:
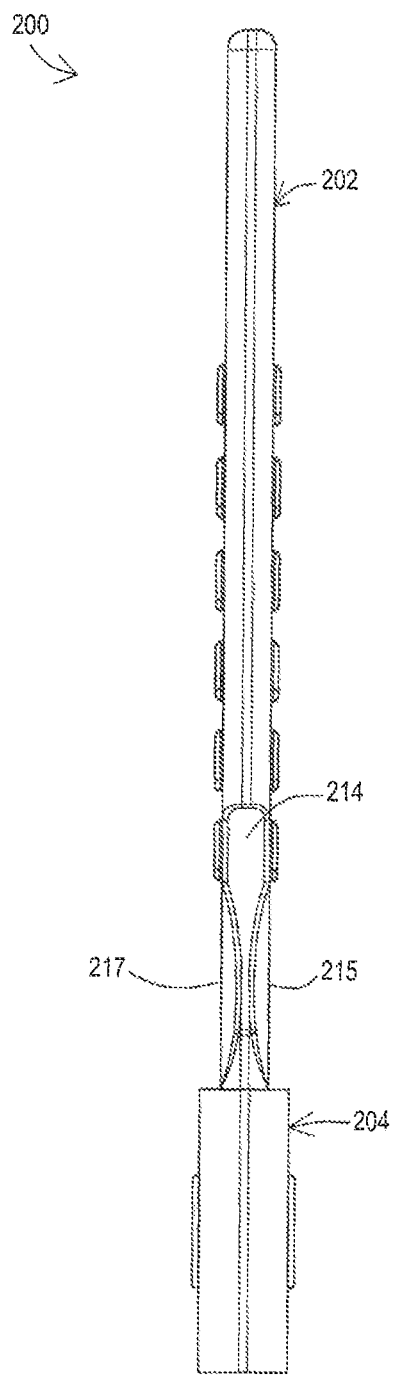
FIG. 10 shows a top view of the second example with the clip in the closed position.

FIG. 7 shows another example of an anchor tool 200 in a closed position. This example includes a first body 202 and a second body 204 that is slidably coupled to the first body 202. The first body 202, second body 204, as well as a blade 208 of the tool 200 may be constructed of the same materials discussed above for the anchor tool 100. The first body 202 defines a handle that the user may grasp, in this case with an arcuate shape but other shapes are also possible. In this example, the first body 202 includes protrusions 216 as well an edge indentation 214 and side indentations 215, 217 to allow the user to have an adequate grip while sliding the tool 200 along the lead. FIG. 10 is a top view that further illustrates the edge indentation 214 and the aligned side indentations 215 and 217 that are present within the first body 204 of this example.

The first body 202 includes a guide portion 210 that defines a lead passageway 212 that the lead may pass through. A blade 208 is exposed from the first body 202 and forms a plane that intersects with the guide portion 210 so as to cut through the anchor. The guide portion 210 can be opened to reveal the lead passageway 212 by movement of the second body 204 relative to the first body 202.

Figure 8:
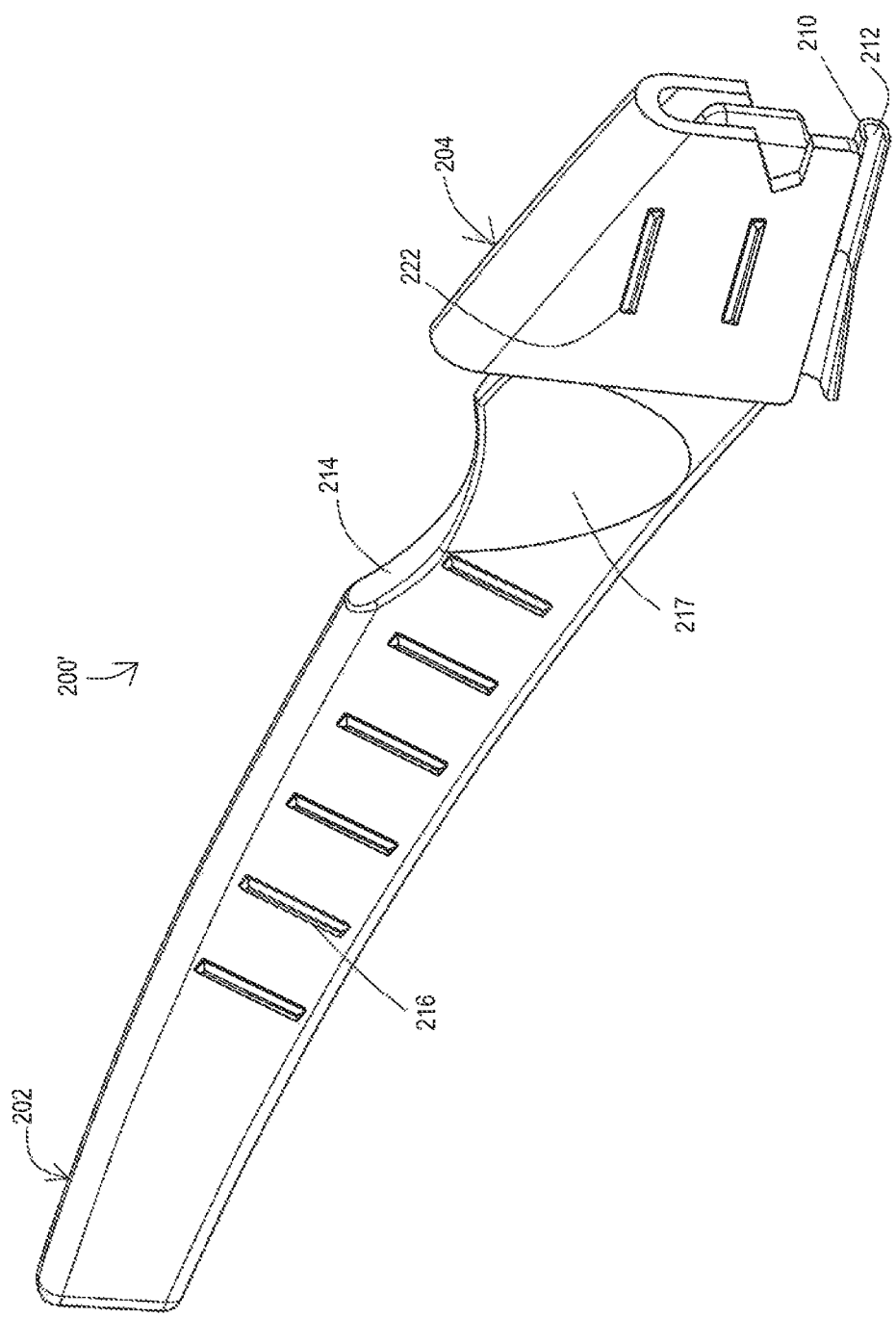
FIG. 8 shows an opposite side view of the second example with the clip in an open position.

The second body 204 is attached to the first body 202 such that when the second body 204 is in a closed position as shown in FIG. 7, the second body 204 closes the opening in the guide portion 210 to the lead passageway 212. The user can slide the second body 204 upward in this example to expose the opening in the guide portion 210 as shown in FIG. 8 which allows the lead to be inserted along the longitudinal opening. For instance, the lead may be moved laterally, and hence at any available location along the lead body, into the lead passageway 212 through the longitudinal opening in the guide portion 210. The user can then slide the second body 204 downward in this example to the closed position shown in FIG. 7 to contain the lead within the lead passageway while allowing the tool 200 to slide along the lead.

Figure 9:
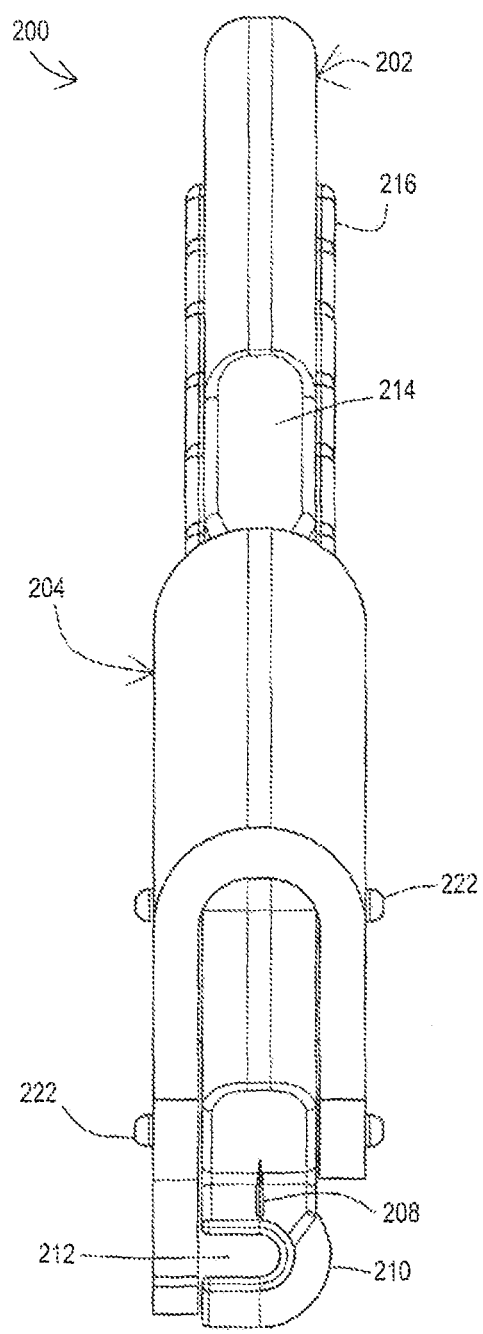
FIG. 9 shows a front view of the second example with the clip in the closed position.

The relationship of the second body 204 to the guide portion 210 and the lead passageway 212 can be further seen in the front view of FIG. 9. Here the second body 204 is in the closed position to enclose the lead passageway 212. In this example, the second body 204 includes protrusions 222 which provide additional grip for the user when grasping the second body 204 in order to raise or lower the second body 204 relative to the first body 202. The protrusions 222 may be present on both sides of the second body 204 as shown in FIG. 9 so that there is additional grip for both fingers pinching the second body 204 to raise or lower to the second body 204.

Figure 11:
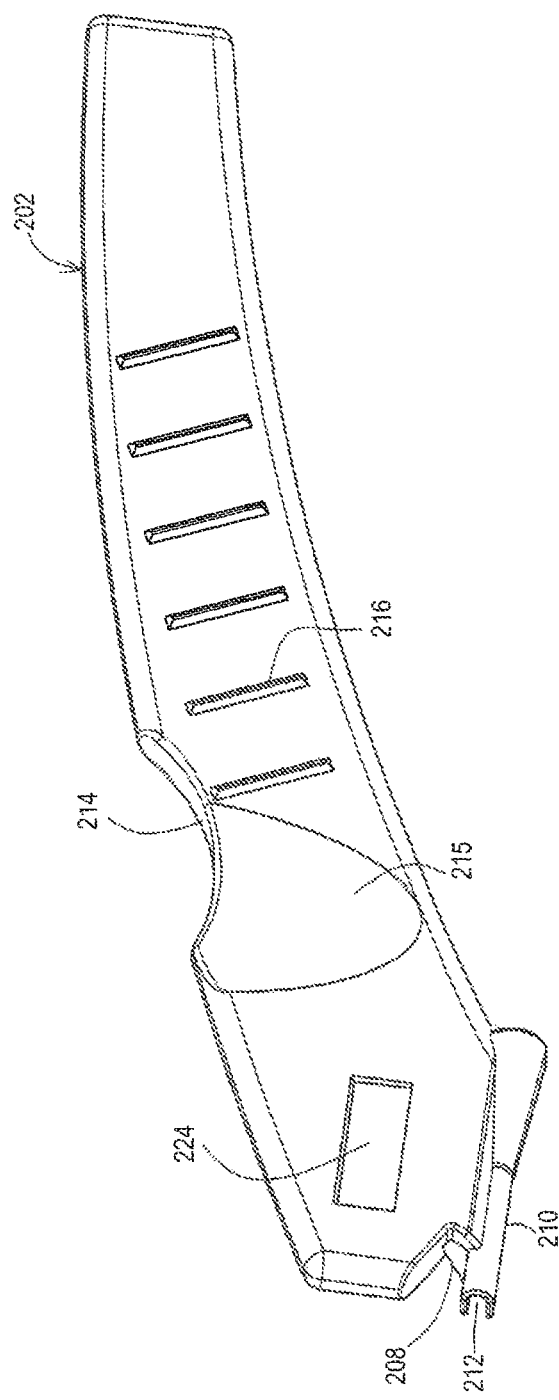
FIG. 11 shows a side view of the second example with clip omitted.

FIG. 11 shows the first body 202 with the second body 204 removed for purposes of illustration. The first body 202 includes a recess 224 in the area where the second body 204 is normally present. The recess 224, which may be present in the same area on both sides of the first body 202, provides a structure for attachment of the second body 204. Additionally, the recess 224 may constrain the sliding movement of the second body 204 relative to the first body 202. The recess 224 may also include features, such as horizontal grooves at stop positions to hold the second body 204 at a fixed position, such as open or closed, until forced to the opposite position by the user. Other structures may also be used for attachment of the second body 204. For instance, the second body 204 could be attached to the first body 202 by a hinge such that the second body 204 pivots forward to open the lead passageway 212.

Figure 12:
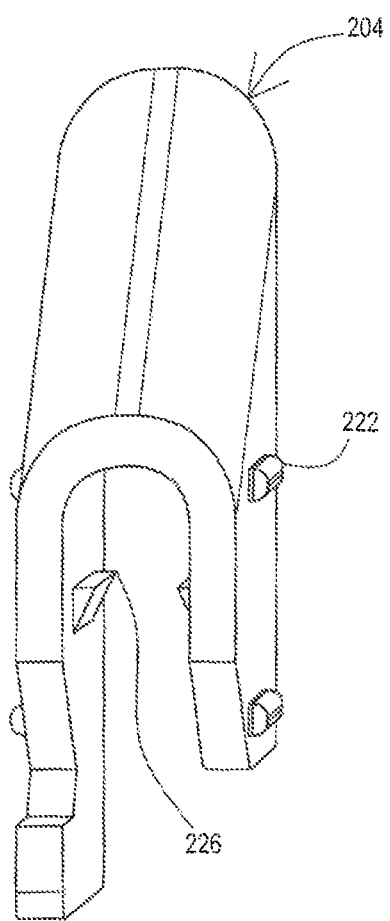
FIG. 12 shows a front view of the clip.

FIG. 12 shows a front view of the second body 204. This front view reveals inner protrusions 226 that are present on the inner walls of the second body 204. These inner protrusions 226 engage the recess 224 of the first body 202 as shown in FIG. 11 in order to retain the second body 204 on the first body 202 and to define the path of movement of the second body 204 relative to the first body 202. To the extent the recess 224 may have features to provide stop positions to hold the second body 204 in place, the protrusions 226 may engage those features to hold the second body 204 in place until forced to the opposite position by the user.

Figure 13:
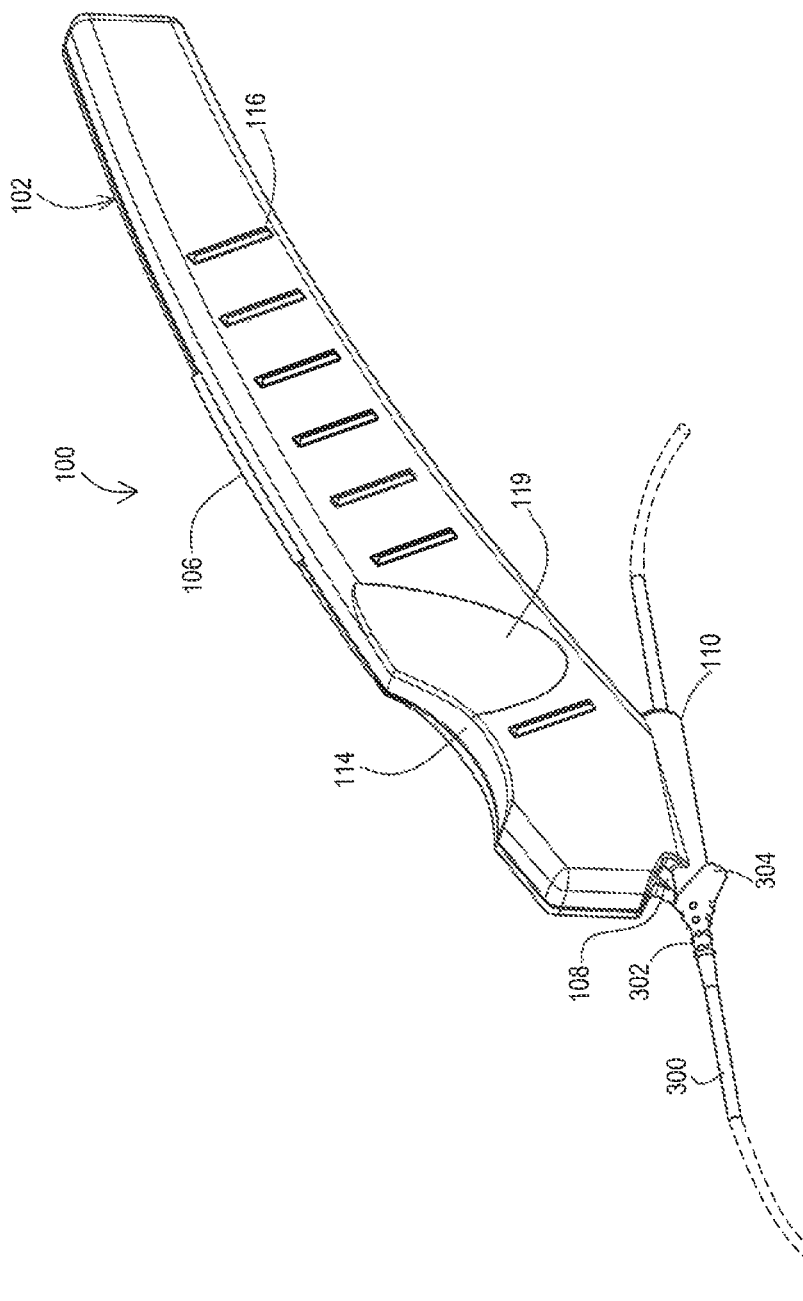
FIG. 13 shows a side view of the first example being used to remove an anchor from a lead.

FIG. 13 shows the operation of the anchor tool 100. At this point, the lead 300 has been inserted into the lead passageway 112 of the anchor tool 100 which is now closed. The lead 300 may have been inserted by feeding a free end of the lead 300 into the end of the lead passageway 112 if a free end is available. Alternatively, the lead 300 may be introduced at any available location along the lead by insertion along the longitudinal opening of the guide portion 110 while the anchor tool 100 is hinged open. For instance the lead 300 may be moved laterally through the longitudinal opening of the guide portion 110. The anchor tool 100 is then closed to contain the lead 300 within the lead passageway 112.

The anchor tool 100 is then slid along the lead until encountering the anchor 302. Upon encountering the anchor 302, the anchor 302 begins to slide onto the leading edge of the guide portion 110 and encounters the blade 108 which slices through the anchor 302. If the anchor is still sutured in place, the sutures may also be cut by the blade 108. The sliced open portion 304 of the anchor 302 then peels away from the lead 300 as the anchor tool 100 continues to slide along the lead 300 until cutting through the entire length of the anchor 302. At that point the anchor 302 is no longer present on the lead and the anchor tool 100 can be removed by the tool 100 being hinged open and pulling the lead 300 out through the longitudinal opening, such as by laterally moving the lead 300 with the tool 100 at any point along the lead 300. Alternatively, the anchor tool 100 can be slid along the lead 300 in either direction and off of a free end if one is available.

FIG. 14 shows the operation of the anchor tool 200. At this point, the lead 300 has been inserted into the lead passageway 212 of the anchor tool 200 which is now closed. The lead 300 may have been inserted by feeding a free end of the lead 300 into the end of the lead passageway 212 if a free end is available. Alternatively, the lead 300 may be introduced at any available location along the lead by insertion along the longitudinal opening of the guide portion 210 while the anchor tool 200 is open by sliding the second body 204. For instance the lead 300 may be moved laterally through the longitudinal opening of the guide portion 210. The anchor tool 200 is then closed by sliding down the second body 204 to contain the lead 300 within the lead passageway 212.

The anchor tool 200 is then slid along the lead until encountering the anchor 302. Upon encountering the anchor 302, the anchor 302 begins to slide onto the leading edge of the guide portion 210 and encounters the blade 208 which slices through the anchor 302. If the anchor is still sutured in place, the sutures may also be cut by the blade 208. The sliced open portion 304 of the anchor 302 then peels away from the lead 300 as the anchor tool 200 continues to slide along the lead 300 until cutting through the entire length of the anchor 302. At that point the anchor 302 is no longer present on the lead 300 and the anchor tool 200 can be removed by the second body 204 being moved upward relative to the first body 202 and pulling the lead 300 out through the longitudinal opening, such as by laterally moving the lead 300 with the tool 200 at any point along the lead 300. Alternatively, the anchor tool 200 can be slid along the lead 300 in either direction and off of a free end if one is available.

While embodiments have been particularly shown and described, it will be understood by those skilled in the art that various other changes in the form and details may be made therein without departing from the spirit and scope of the invention.

What is claimed is:

1. An implantable medical lead anchor removal tool, comprising:
   a first body including a guide portion having an inner lead passageway having a longitudinal dimension defined along the length of the guide portion;
   a second body movably coupled to the first body by a coupling providing an axis of rotation of the second body relative to the first body where the axis of rotation is parallel to the longitudinal dimension from at least one perspective perpendicular to the longitudinal dimension, the second body having a protrusion that is present within the inner lead passageway, the inner lead passageway being opened along the longitudinal dimension when the second body is moved relative to the first body about the axis of rotation of the coupling to thereby remove the protrusion of the second body from the inner lead passageway, wherein at least one of the first body and the second body provides an elongated portion including an arcuate top edge and an arcuate bottom edge where a radius of curvature of both the arcuate top edge and the arcuate bottom edge has a center point spaced from the bottom edge in a direction away from the top edge and wherein the arcuate top edge and the arcuate bottom edge span more than half of a length of the elongated portion; and a blade present within the first body, the blade having a cutting edge that is at least partially exposed from the first body and that is aligned so that a plane defined by the blade intersects with the guide portion in the first body such that the blade contacts the guide portion where the guide portion forms the inner lead passageway and with the entire blade being outside of the inner lead passageway.

2. The implantable medical lead anchor of claim 1, wherein the coupling comprises a hinged coupling and wherein the first body and the second body are hingedly coupled such that the second body rotates at the hinged coupling to move relative to the first body.

3. The implantable medical lead anchor of claim 2, wherein the first body, the second body, and the hinged coupling are integral to a tool body.

4. The implantable medical lead anchor removal tool of claim 2, further comprising an edge indentation in a first edge of the first body and an edge indentation in a first edge of the second body, wherein the edge indentation in the first body and the edge indentation in the second body become aligned and form a common edge indentation when the first body and the second body are brought together by rotation at the hinged coupling.

5. The implantable medical lead anchor removal tool of claim 2, further comprising a side indentation in a first side of the first body and a side indentation in a first side of the second body, wherein the side indentation of the first body and the side indentation of the second body become aligned when the first body and the second body are brought together by rotation about the hinged coupling.

6. The implantable medical lead anchor removal tool of claim 1, further comprising:

a plurality of protrusions present on an outer surface of the first body and the second body, the protrusions being oriented at an angle relative to the longitudinal dimension of the guide portion.

7. The implantable medical lead anchor removal tool of claim 1, wherein both the first body and the second body have top and bottom edges that are arcuately shaped.

8. The implantable medical lead anchor removal tool of claim 1, further comprising:

a plurality of protrusions present on opposing outer surfaces of the first body, the protrusions being oriented at an angle relative to the longitudinal dimension of the guide portion.

9. The implantable medical lead anchor removal tool of claim 1, further comprising an edge indentation in a first edge of the first body.

10. The implantable medical lead anchor removal tool of claim 1, further comprising a side indentation in opposing sides of the first body.

11. The implantable medical lead anchor removal tool of claim 1, wherein the first body has the top edge and the bottom edge that are arcuately shaped.

12. The implantable medical lead anchor removal tool of claim 1, further comprising a plurality of protrusions present on opposing outer surfaces of the second body.

13. The implantable medical lead anchor removal tool of claim 1, wherein the inner lead passageway has an opening at both ends with each opening being present when the second body moves relative to the first body.

* * * * *